United States Patent [19]

Ito et al.

[11] Patent Number: 4,617,400

[45] Date of Patent: Oct. 14, 1986

[54] PROCESS FOR PREPARING CYCLIC UREA DERIVATIVES

[75] Inventors: Kazuhisa Ito, Fujimi; Yoshio Fukuda, Kawagoe, both of Japan

[73] Assignee: Kawaken Fine Chemicals Co., Ltd., Tokyo, Japan

[21] Appl. No.: 774,986

[22] Filed: Sep. 11, 1985

[51] Int. Cl.$^4$ ............................................. C07D 233/32
[52] U.S. Cl. ..................................... 548/317; 544/315
[58] Field of Search ........................ 548/317; 544/315

[56] References Cited

U.S. PATENT DOCUMENTS 2,422,400  6/1947  Farlow ................................ 548/317

FOREIGN PATENT DOCUMENTS 52-71419  6/1977  Japan ................................... 548/317
60-03299  1/1985  Japan ................................... 548/317

OTHER PUBLICATIONS

*Chemical Abstracts,* 83:43789v (1975) [Yamamura, T., et al., *Nippon Kagaku Kaishi,* 1975, (3), 427–31].
*Chemical Abstracts,* 90:72186w (1979) [Jpn. Kokai, 78, 98, 965, 8/29/78].

*Primary Examiner*—Richard A. Schwartz
*Attorney, Agent, or Firm*—McAulay, Fields, Fisher, Goldstein & Nissen

[57] ABSTRACT

A process for preparing a cyclic N,N'-dimethyl urea derivative by reacting a cyclic urea compound with formaldehyde, in a medium, in the presence of hydrogen and a hydrogenation catalyst. The reaction is carried out in the presence of a solid acid obtained by calcining sulfuric acid and aluminum oxide or sulfuric acid, phosphoric acid and aluminum oxide.

8 Claims, No Drawings

PROCESS FOR PREPARING CYCLIC UREA DERIVATIVES

BACKGROUND OF THE INVENTION (1) Field of the Invention

The present invention relates to a process for preparing cyclic urea derivatives. More particularly, the present invention relates to an industrially advantageous process for the preparation of a cyclic N,N'-dimethyl urea derivatives by reacting a cyclic urea compound with formaldehyde or paraformaldehyde.

(2) Description of the Related Art

Cyclic N,N'-dimethyl urea derivatives are important polar non-proton solvents and are widely used as medium for organic synthetic reactions, solvent for polymeric compounds, solvent for the extraction of aromatic hydrocarbons and unsaturated hydrocarbons in the petrolium refining, and the like. Thus, they are industrially very useful compounds.

The following processes are known as a conventional process for the preparation of a cyclic N,N'-dimethyl urea derivative.

(1) Process as described in U.S. Pat. No. 2,422,400

The process is comprised of two steps of (a) forming a methylol intermediate from 2-imidazolidinone and formaldehyde in an alkaline medium and isolating it and of (b) adjusting the pH of the reaction medium followed by the catalytic reduction.

(2) Process as described in Japanese Unexamined Patent Publication (Kokai) No. 52-71419

1,3-Dimethyl-2-imidazolidinone is prepared from 2-imidazolidinone and formaldehyde in one step by hydrogenation in a acidic medium of a pH of 3 to 5. In this publication, it is not specified and thus not clear what substance is used for acidifying the reaction mixture. However, in Example 1, there is described a process in which the reaction mixture is adjusted to pH of 3 by adding phosphoric acid. For the practice of the process, it is inevitably necessary to use a non-corrodible reaction apparatus, and in addition a salt which is difficult to be separated is produced by the neutralization of the reaction mixture after the completion of the reaction.

(3) Process as described in Japanese Examined Patent Publication (Kokoku) No. 60-3299

1,3-Bis-(hydroxymethyl)- or 1,3-bis-(alkoxymethyl)-2-imidazolidinone is reduced, in the presence of an acidic substance, using a hydrogenation catalyst. However, in order to prepare 1,3-bis-(hydroxymethyl)- or 1,3-bis-(alkoxymethyl)-2-imidazolidinone, it is necessary to prepare a methylol intermediate from 2-imidazolidinone and formaldehyde as in the process described in the above-mentioned U.S. Pat. No. 2,422,400, which indicates that the process substantially consists of two steps. Further, since it is necessary to carry out the catalytic reduction in the presence of an acidic substance at a pH of not higher than 3, a non-corrodible apparatus should be used and further a salt produced by neutralization after the completion of the reaction must be separated, as in the process described in the above-mentioned Japanese Unexamined Patent Publication No. 52-71419.

As mentioned above, the conventional processes for the preparation of cyclic N,N'-dimethyl urea derivatives are not satisfactory for the industrial purposes.

SUMMARY OF THE INVENTION

The present inventors made extensive studies for establishing a process for the preparation of cyclic N,N'-dimethyl urea derivatives under a mild condition under which the process can be industrially practiced, and found that specific solid acids are useful for such a process. As the results, the inventors attained the present invention.

Thus, the present invention provides a process for preparing a cyclic N,N'-dimethyl urea derivative of formula I,

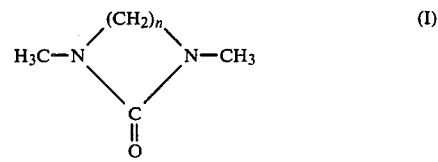

in which n is 2 or 3, by reacting a cyclic urea compound of formula II,

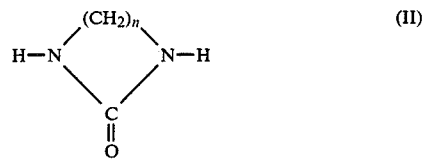

in which n is as defined above, with formaldehyde, in a medium, in the presence of hydrogen and a hydrogenation catalyst, characterized in that said reaction is carried out in the presence of at least one member selected from the group consisting of solid acids obtained by calcining sulfuric acid or its ammonium salt and aluminum oxide and by calcining sulfuric acid or its ammonium salt, phosphoric acid or its ammonium salt and aluminum oxide.

DESCRIPTION OF THE PREFERRED EMBODIMENTS

The subject compounds of the present invention are the cyclic urea derivatives represented by the above-mentioned formula I, and may include 1,3-dimethyl-2-imidazolidinone and N,N'-dimethyl-propylene urea. As the compounds represented by the above formula II, there may be mentioned 2-imidazolidinone and propylene urea.

The solid acids useful for the present invention may include a solid acid obtained by calcining sulfuric acid or its ammonium salt and aluminum oxide and a solid acid obtained by calcining sulfuric acid or its ammonium salt, phosphoric acid or its ammonium salt and aluminum oxide. The object of the present invention can be attained by the use of either of the two solid acids or both. The ratio of the atoms constituting the solid acids may be in a range of 0.01 to 0.06 as S/Al in the case of sulfate ion and aluminum oxide, and in ranges of 0.02 to 0.2 as (P+S)/Al and 0.02 to 0.8 as S/P in the case of sulfate ion, phosphate ion and aluminum oxide. Where the ratios of the solid acid-constituting atoms are in these ranges, the resulting solid acids have good activity and selectivity.

The solid acids useful for the process of the present invention may be prepared by adding aluminum oxide to an aqueous solution containing sulfate ion or sulfate ion and phosphate ion, prepared by dissolving sulfuric acid, phosphoric acid or an ammonium salt thereof, mixing them well, and then drying and calcining the mixture. Where the solid acid is to be prepared from sulfate ion and aluminum oxide, there may be carried out another process in which aluminum oxide is brought into contact with an aqueous solution containing sulfate ion and then filtered, and the resulting solid is calcined.

The calcining temperature for the preparation of the solid acid may be not lower than 300° C., preferably 500° to 900° C., and the calcining time may be 1 to 10 hours, preferably 2 to 4 hours. The resulting solid acid may be used for the process of the present invention as it stands or after it is boiled with water in an amount of 2 to 10 times the amount of the solid acid, filtered and then washed with water. Aluminum oxide to be used for the preparation of the solid acid is not critical, but gamma-alumina in a powder or bead form is practically preferred.

Formaldehyde or paraformaldehyde to be used for the process of the present invention may be utilized for the reaction as an aqueous solution or methanol solution, suitably in an amount 2 to 4 mols per mol of the cyclic urea compound.

The hydrogenation catalyst may be any hydrogenation catalyst obtainable from palladium, nickel or platinum. However, the hydrogenation catalyst is preferably selected from palladium-carbon, reduced nickel and platinum-carbon catlysts, particularly palladium-carbon catalyst. The catalyst may preferably be used in an amount of 0.1 to 10% by weight based on the weight of the cyclic urea compound.

The solid acid may suitably be used in an amount of 1 to 10% by weight based on the weight of the starting cyclic urea compound, and water or alcholic solvents may suitably be used as the reaction medium. Excess of the cyclic urea compounds of formula I may also be used as the reaction medium. The reaction temperature may be 100° to 200° C., preferably 140° to 170° C., and the pressure of hydrogen upon the catalytic reduction may be 20 to 150 kg/cm$^2$, preferably 40 to 100 kg/cm$^2$.

In the solid acid in the present invention, no sulfur compound is evolved upon the calcining, and sulfur and phosphorous compounds are confirmed to be incorporated in the composition thereof from the weight of the calcined product or the like. The solid acid is not reduced in its activity in the reaction in the process of the present invention even if repeating 5 times a procedure in which the solid acid is boiled with water in an amount of 4 times the amount thereof for 2 hours, filtered and then washed with water, and even further calcining it at a high temperature of 900° C. for 3 hours. Further, the solid acid can be used repeatedly 5 times for the reaction according to the present invention. Thus, it may be considered that there is no or little elimination of sulfur or phosphor compound from the solid acid upon the heating or washing with water.

A characteristic feature of the present invention is that the reaction is carried out under a neutral condition of a pH of 6 to 7. Thus, since the pH of the reaction mixture is approximately neutral during the reaction and after the completion of the reaction, there is no problem of corrosion of the reaction apparatus used, and no neutralization of the reaction mixture after the completion of the reaction is necessary. Therefore, a cyclic N,N'-dimethyl urea derivative of a high purity can be obtained by a simple procedure in that after the completion of the reaction, the solid acid and hydrogenation catalyst are filtered off and the reaction mixture is then subjected to distillation. After the completion of the reaction, the solid acid and hydrogenation catalyst recovered by the filtration can be reused for the subsequent reaction as such without being separated from each other. Therefore, the process of the present invention is very industrially advantageous.

The present invention will be further illustrated by the following examples, in which all temperatures are by degrees Centrigrade.

EXAMPLE 1

(Preparation of Solid Acid)

So as to attain an atomic ratio S/Al of 0.03, 5 g of 98% sulfuric acid was added to 100 ml of water and then 100 g of gamma-alumina was added to the solution. Then, the mixture was dried by evaporation under vacuum on an evaporator, and calcined in air at 500° for 3 hours to obtain 102 g of an solid acid. The solid acid had numerous acid points exhibiting an acid intensity of a Hammett's acidity function (hereinafter referred to as Ho) of not more than $-8.2$. No evolution of sulfur compound was observed during the calcining in the above-mentioned procedure.

EXAMPLE 2

(Preparation of Solid Acid)

100 g of gamma-alumina powder was added to 500 ml of 1 N aqueous sulfuric acid solution and the mixture was stirred for 1 hour and filtered. The gamma-alumina powder filtered off was dried and calcined in air at 500° for 3 hours to obtain 102 g of a solid acid. On the other hand, the filtrate was subjected to titration to determine the sulfate ion concentration in the filtrate. The reduced amount of sulfate ion was calculated from the sulfate ion concentration and the atomic ratio S/Al of the solid acid was estimated to be 0.03. The solid acid had numerous acid points exhibiting an acid intensity of a Ho of less than $-8.2$. No evolution of sulfur compound was observed during the calcining.

EXAMPLE 3

(Preparation of Solid Acid)

So as to attain an atomic ratio (S+P)/Al of 0.11 and an atomic ratio S/P of 0.41, 5 g of 98% sulfuric acid and 12.5 g of 80% phosphoric acid were dissolved in 100 ml of water and to the solution, 100 g of gamma-alumina was added while stirring. Then, the mixture was dried by evaporation under vacuum on an evaporator and calcined in air at 500° for 3 hours to obtain 108 g of a solid acid. The solid acid had numerous acid points exhibiting an acid intensity of a Ho of less than $-8.2$. No evolution of sulfuric acid was observed during the calcining.

EXAMPLE 4

(Preparation of Solid Acid)

So as to attain atomic ratios (S+P)/Al of 0.09 and S/P of 0.16, 2 g of 98% sulfuric acid and 12.5 g of 80% phosphoric acid were dissolved in 100 ml of water and 100 g of gamma-alumina was added to the solution while stirring. The mixture was then treated as in Example 3 to obtain 107 g of a solid acid. The solid acid had numerous acid points exhibiting an acid intensity of a Ho of less than $-8.2$. No evolution of sulfur compound was observed during the calcining.

EXAMPLE 5

(Preparation of Solid Acid)

6.7 g of ammonium sulfate and 6.25 g of 80% phosphoric acid were dissolved in 100 ml of water and 100 g of gamma-alumina was added to the solution. After drying by evaporation under vacuum, the mixture was calcined in air at 500° for 3 hours to obtain 108 g of a solid acid. The solid acid had atomic ratios of a (S+P)/Al of 0.06 and a S/P of 0.96. The solid acid had numerous acid points exhibiting an acid intensity of a Ho of less than −8.2. No evolution of sulfur compound was observed during the calcining.

EXAMPLE 6

(Preparation of Solid Acid)

To 100 g of the solid acid obtained as in Example 3, 300 ml of water was added, and the mixture was boiled for 2 hours, filtered and then washed with water. The same procedure was further repeated 4 times, and the mixture was dried and calcined in air at 900° for 3 hours to obtain 99 g of a solid acid. The solid acid had a Ho of less than −8.2 and no evolution of sulfur compound was observed during the calcining.

EXAMPLE 7

(Preparation of Solid Acid)

To 100 g of the solid acid obtained as in Example 3, 300 ml of water was added and the mixture was boiled for 30 minutes, filtered and washed with water. The same procedure was repeated further 2 times, the mixture was dried to obtain 106 g of a solid acid.

EXAMPLE 8

33.1 g of 2-imidazolidinone(purity 86.3%, water content 13.5%) was dissolved in 40 ml of methanol, 0.7 g of activated carbon was added to the solution and the mixture was stirred at 40° to 50° for 30 minutes. After the activated carbon was filtered off, the mixture was charged into an autoclave together with 47.8 g of 46% formaldehyde(methanol 44%, water 10%), 2 g of the solid acid obtained as in Example 1 and 1 g of 5% palladium-carbon, hydrogen was introduced after hydrogen purging and then the mixture was allowed to react at 140° to 150° and 40 to 80 kg/cm² for 4 hours. After the completion of the reaction, the content was removed and the catalyst and solid acid were filtered off. The pH of the filtrate was determined using a pH meter to be 6.1. Water and methanol were distilled off from the filtrate. The filtrate was then subjected to distillation under reduced pressure to obtain 32.3 g of 1,3-dimethyl-2-imidazolidinone at 120°/25 mmHg. The yield was 85.0%, and the purity was 99% as determined by gas chromatography.

EXAMPLES 9 to 14

The procedure as in Example 8 was repeated using each of the solid acids as prepared in Examples 2 to 7. The obtained results are shown in Table 1 below.

TABLE 1

| | Solid acid | pH of reaction mixture after reaction | Yield % | Purity % |
| --- | --- | --- | --- | --- |
| Example 9 | Example 2 | 6.3 | 84.5 | 99 |
| Example 10 | Example 3 | 6.7 | 92.9 | 99 |
| Example 11 | Example 4 | 7.1 | 89.0 | 99 |
| Example 12 | Example 6 | 6.8 | 92.3 | 99 |
| Example 13 | Example 5 | 6.7 | 92.6 | 99 |
| Example 14 | Example 7 | 6.0 | 95.2 | 99 |

EXAMPLE 15

30.0 g of propylene urea(tetrahydro-2-pyrimidinone) was dissolved in 50 ml of methanol, 0.7 g of activated carbon was added to the solution and the mixture was stirred at 40° to 50° for 30 minutes. After filtering off the activated carbon, the mixture was added with 43.0 g of 46% formaldehyde-methanol solution, 1.5 g of 5% palladium-carbon and 3.0 g of the solid acid prepared as in Example 3, and the mixture was then charged into an autoclave and reacted under a hydrogen pressure of 40 to 80 kg/cm² at a temperature of 140° to 150° for 4 hours. After the completion of the reaction, the content was removed and the catalyst and solid acid were filtered off. The pH of the filtrate was 6.2 and no corrosion was observed on the autoclave. Water and methanol were distilled off and the residue was distilled under reduced pressure to obtain 33.4 g (yield 87.0%) of N,N'-dimethyl-propylene urea at 124°/20 mmHg. The purity was 99% as measured by gas chromatography.

EXAMPLES 16 to 18

0.3 g of the solid acid prepared as in Example 6 and 0.16 g of 5% palladium-carbon were added to the mixture of the solid acid and catalyst recovered from the reaction mixture of Example 12. The mixture was then treated according to the procedure as in Example 1 to prepare 1,3-dimethyl-2-imidazolidinone.

Further, using the recovered catalyst, the reaction for the preparation of 1,3-dimethyl-2-imidazolidinone was repeatedly carried out. The results are shown in Table 2 below.

TABLE 2

| | pH of reaction mixture after reaction | Yield % | Purity % | Remark |
| --- | --- | --- | --- | --- |
| Example 16 | 6.1 | 94.6 | 99 | Repitition of Example 12 |
| Example 17 | 6.4 | 94.2 | 99 | Repitition of Example 16 |
| Example 18 | 6.1 | 92.8 | 99 | Repitition of Example 17 |

EXAMPLE 19

Using 2 g of the solid acid prepared as in Example 3 and 1.0 g of 5% platinum-carbon catalyst, 1,3-dimethyl-2-imidazolidinone was prepared according to the procedure as in Example 8. The reaction proceeded for 8 hours and 28.8 g (yield 76.0%) of 1,3-dimethyl-2-imidazolidinone was obtained. The purity was 99%.

EXAMPLE 20

(Corrosion Test)

Two test pieces of SUS 316 and SUS 316 L having a size of 30 mm×50 mm×2 mm were immersed into a reaction mixture having a composition analogous to that of Example 8 at 160° for 120 hours for corrosion test. The weights of the pieces were measured before and after the corrosion test and proved to be almost unaltered. The analysis of the nickel and iron contents in the reaction mixture proved to be 2.2 ppm. and 1.5 ppm, respectively, which showed that the corrosion could be ignored.

We claim:

1. A process for preparing a cyclic N,N'-dimethyl urea derivative of formula I,

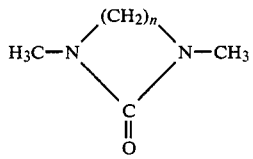
(I)

in which n is 2 or 3, by reacting a cyclic urea compound of formula II,

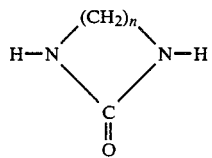
(II)

in which n is as defined above, with formaldehyde, in a medium, in the presence of hydrogen and a hydrogenation catalyst, characterized in that said reaction is carried out in the presence of at least one member selected from the group consisting of solid acids obtained by calcining sulfuric acid or its ammonium salt and aluminum oxide and by calcining sulfuric acid or its ammonium salt, phosphoric acid or its ammonium salt and aluminum oxide.

2. A process as claimed in claim 1, wherein the compound of formula I is 1,3-dimethyl-2-imidazolidinone.

3. A process as claimed in claim 1, wherein the solid acid has an atomic ratio S/Al of 0.01 to 0.06 in the case of one obtained from sulfate and aluminum oxide.

4. A process as claimed in claim 1, wherein the solid acid has atomic ratios (S+P)/Al of 0.02 to 0.2 and S/P of 0.02 to 0.8 in the case of one obtained from sulfate, phosphate and aluminum oxide.

5. A process as claimed in claim 1, wherein the solid acid is selected from those obtained by dispersing aluminum oxide into an aqueous solution containing sulfate ion or sulfate ion and phosphate ion, and after subjecting the dispersion to evaporation to dryness or filtration and drying, calcining the dried mixture.

6. A process as claimed in claim 1, wherein the solid acid is used in an amount of 1 to 10% by weight based on the weight of the cyclic urea compound of formula II.

7. A process as claimed in claim 1, wherein the hydrogenation catalyst is selected from those obtained from palladium, platinum and nickel.

8. A process as claimed in claim 1, wherein the reaction medium is selected from water, lower alcohol compounds and the cyclic urea compounds used for the reaction.

* * * * *